(12) United States Patent
Taylor

(10) Patent No.: US 6,739,531 B2
(45) Date of Patent: May 25, 2004

(54) APPARATUS AND METHOD FOR RAPID DISRUPTION OF CELLS OR VIRUSES

(75) Inventor: Michael T. Taylor, Newark, CA (US)

(73) Assignee: Cepheid, Sunnyvale, CA (US)

( * ) Notice: Subject to any disclaimer, the term of this patent is extended or adjusted under 35 U.S.C. 154(b) by 70 days.

(21) Appl. No.: 09/972,221

(22) Filed: Oct. 4, 2001

(65) Prior Publication Data

US 2003/0066915 A1 Apr. 10, 2003

(51) Int. Cl.$^7$ .............................................. B02C 19/18
(52) U.S. Cl. ................. 241/1; 241/2; 241/301
(58) Field of Search .................. 435/6, 173.7, 259; 241/2, 1, 301

(56) References Cited

U.S. PATENT DOCUMENTS 6,431,476 B1 * 8/2002 Taylor et al. .................. 241/1

* cited by examiner

Primary Examiner—Mark Rosenbaum
(74) Attorney, Agent, or Firm—Townsend and Townsend and Crew LLP

(57) ABSTRACT

An apparatus for disrupting cells or viruses comprises a container having a chamber for holding the cells or viruses. The chamber is defined by at least one wall having an external surface for contacting a transducer device. The transducer device has a vibrating surface for contacting the wall and for vibrating at an operating frequency and amplitude sufficient to generate pressure waves or pressure pulses in the chamber. The transducer device is coupled to the wall with a preload force sufficient to create a stress within the wall. The natural frequency of the wall, when the wall is stressed by the preload force, is equal to the operating frequency of the transducer device or differs from the operating frequency by less than 50% of the operating frequency.

30 Claims, 8 Drawing Sheets

APPARATUS AND METHOD FOR RAPID DISRUPTION OF CELLS OR VIRUSES

FIELD OF THE INVENTION

The present invention relates to an apparatus and method for rapidly disrupting cells or viruses.

BACKGROUND OF THE INVENTION

The extraction of nucleic acid from cells or viruses is a necessary task for many applications in the fields of molecular biology and biomedical diagnostics. Once released from the cells, the nucleic acid may be used for genetic analysis, e.g., sequencing, pathogen identification and quantification, nucleic acid mutation analysis, genome analysis, gene expression studies, pharmacological monitoring, storing of DNA libraries for drug discovery, etc. The genetic analysis typically involves nucleic acid amplification and detection using known techniques. For example, known polynucleotide amplification reactions include polymerase chain reaction (PCR), ligase chain reaction (LCR), QB replicase amplification (QBR), self-sustained sequence replication (3 SR), strand-displacement amplification (SDA), "branched chain" DNA amplification, ligation activated transcription (LAT), nucleic acid sequence-based amplification (NASBA), rolling circle amplification (RCA), repair chain reaction (RCR), and cycling probe reaction (CPR).

The extraction of nucleic acids from cells or viruses is generally performed by physical or chemical methods. Chemical methods typically employ lysing agents (e.g., detergents, enzymes, or strong organics) to disrupt the cells and release the nucleic acid, followed by treatment of the extract with chaotropic salts to denature any contaminating or potentially interfering proteins. Such chemical methods are described in U.S. Pat. No. 5,652,141 to Henco et al. and U.S. Pat. No. 5,856,174 to Lipshutz et al. One disadvantage to the use of harsh chemicals for disrupting cells is that the chemicals are inhibitory to subsequent amplification of the nucleic acid. In using chemical disruption methods, therefore, it is typically necessary to purify the nucleic acid released from the cells before proceeding with further analysis. Such purification steps are time consuming, expensive, and reduce the amount of nucleic acid recovered for analysis.

Physical methods for disrupting cells often do not require harsh chemicals that are inhibitory to nucleic acid amplification (e.g., PCR). These physical methods, however, also have their disadvantages. For example, one physical method for disrupting cells involves placing the cells in a solution and heating the solution to a boil to break open the cell walls. Unfortunately, the heat will often denature proteins and cause the proteins to stick to the released nucleic acid. The proteins then interfere with subsequent attempts to amplify the nucleic acid. Another physical method is freeze thawing in which the cells are repeatedly frozen and thawed until the cells walls are broken. Unfortunately, freeze thawing often fails to break open many structures, most notably certain spores and viruses that have extremely tough outer layers.

Another physical method for disrupting cells is the use of a pressure instrument. With this method, a solution of mycobacterial microorganisms is passed through a very small diameter hole under high pressure. During passage through the hole, the mycobacteria are broken open by the mechanical forces and their internal contents are spilled into solution. Such a system, however, is large, expensive and requires a cooling system to prevent excessive heat from building up and damaging the contents of the lysed cells. Moreover, the instrument needs to be cleaned and decontaminated between runs and a large containment system is required when infectious material is handled. A further disadvantage to this system is that the solution must contain only particles having substantially the same size, so that it may not be used to process many untreated clinical or biological specimens.

It is also known that cells can be lysed by subjecting the cells to ultrasonic agitation. This method is disclosed by Murphy et al. in U.S. Pat. No. 5,374,522. According to the method, solutions or suspensions of cells are placed in a container with small beads. The container is then placed in an ultrasound bath until the cells disrupt, releasing their cellular components. This method has several disadvantages. First, the distribution of ultrasonic energy in the bath is not uniform, so that a technician must locate a high energy area within the bath and place the container into that area. The non-uniform distribution of ultrasonic energy also produces inconsistent results. Second, the ultrasound bath does not focus energy into the container so that the disruption of the cells often takes several minutes to complete, a relatively long period of time when compared to the method of the present invention. Third, it is not practical to carry an ultrasound bath into the field for use in biowarfare detection, forensic analysis, or on-site testing of environmental samples.

Another method for ultrasonic lysis of cells is disclosed in U.S. Pat. No. 4,983,523 to Li. According to the method, nucleic acids are released from cells, bacteria and viruses by non-invasively sonicating a sample contained within a sample container that is brought into physical contact with the vibrating element of a sonicator tuned to resonate at a frequency of 40 kHz or greater. One major problem with contacting a wall of a sample container with the vibrating element of a sonicator is that the vibration of the sonicator against the wall is very likely to cause severe damage to the wall (generally melting or cracking of the wall) leading to contamination of the work area, a health hazard to the operator, and loss of the sample to be analyzed.

SUMMARY

The present invention overcomes the disadvantages of the prior art by providing an improved apparatus and method for disrupting cells or viruses to release the nucleic acid therefrom. The apparatus and method of the present invention provides for the rapid, non-invasive lysis of cells or viruses held in a container by applying the vibrating surface of a transducer device to a wall of the container without melting, cracking, or otherwise damaging the wall of the container.

In a preferred embodiment, the apparatus comprises a container having a chamber for holding a liquid or gel that contains the cells or viruses to be disrupted. The container includes at least one wall defining the chamber, and the wall has a surface external to the chamber for contacting the vibrating surface of a transducer device. The wall thus provides an interface between the contents of the chamber and the vibrating surface of the transducer device. The apparatus also comprises a transducer device having a vibrating surface for contacting the external surface of the wall and for vibrating at an operating frequency and amplitude sufficient to generate pressure waves or pressure pulses in the chamber. The apparatus further comprises means for coupling the surface of the transducer device to the wall with a preload force sufficient to create a stress within the wall. The natural frequency of the wall, when the wall is stressed by the preload force, is equal to the operating frequency of the transducer device or differs from the operating frequency of the transducer device by less than 50% of the operating frequency of the transducer device, and more preferably by less than 25% of the operating frequency of the transducer device.

According to another aspect, the present invention provides a method for disrupting cells or viruses. The method comprises the step of holding a liquid or gel containing the cells or viruses in the chamber of a container. The container includes at least one wall defining the chamber, and the wall has a surface external to the chamber. A transducer device is coupled to the external surface of the wall with a preload force sufficient to create a stress within the wall. The transducer device is operated at a frequency and amplitude sufficient to generate pressure waves or pressure pulses in the chamber. The natural frequency of the wall, when the wall is stressed by the preload force, is equal to the operating frequency of the transducer device or differs from the operating frequency of the transducer device by less than 50% of the operating frequency of the transducer device, and more preferably by less than 25% of the operating frequency of the transducer device.

Since the natural frequency of the chamber wall, when the wall is stressed by the preload force, is tuned to the operating frequency of the transducer device, the wall efficiently transfers the energy from the vibrating surface of the transducer device to the chamber without substantial heat build up at the interface. This permits the efficient transfer of energy to the chamber and the rapid lysis of cells or viruses in the chamber without melting or cracking the container.

DETAILED DESCRIPTION

The present invention provides an apparatus and method for disrupting cells or viruses. The cells may be animal or plant cells, spores, bacteria, or microorganisms. The viruses may be any type of infective agents having a protein coat surrounding an RNA or DNA core.

All publications and patent applications cited in this specification are herein incorporated by reference as if each individual publication or patent application were specifically and individually indicated to be incorporated by reference.

Figure 1:
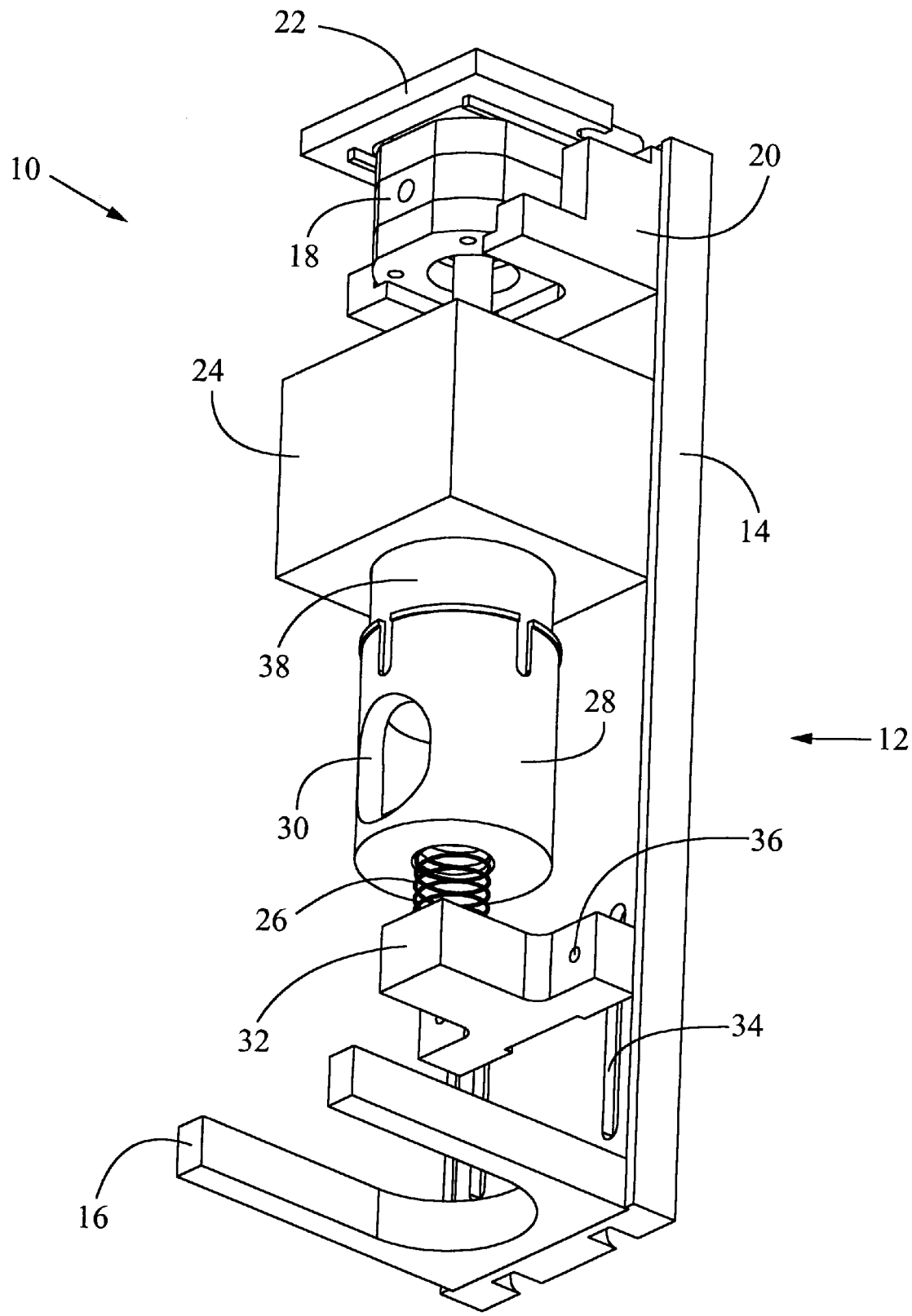
FIG. 1 is an isometric view of an apparatus for disrupting cells or viruses.
Figure 2:
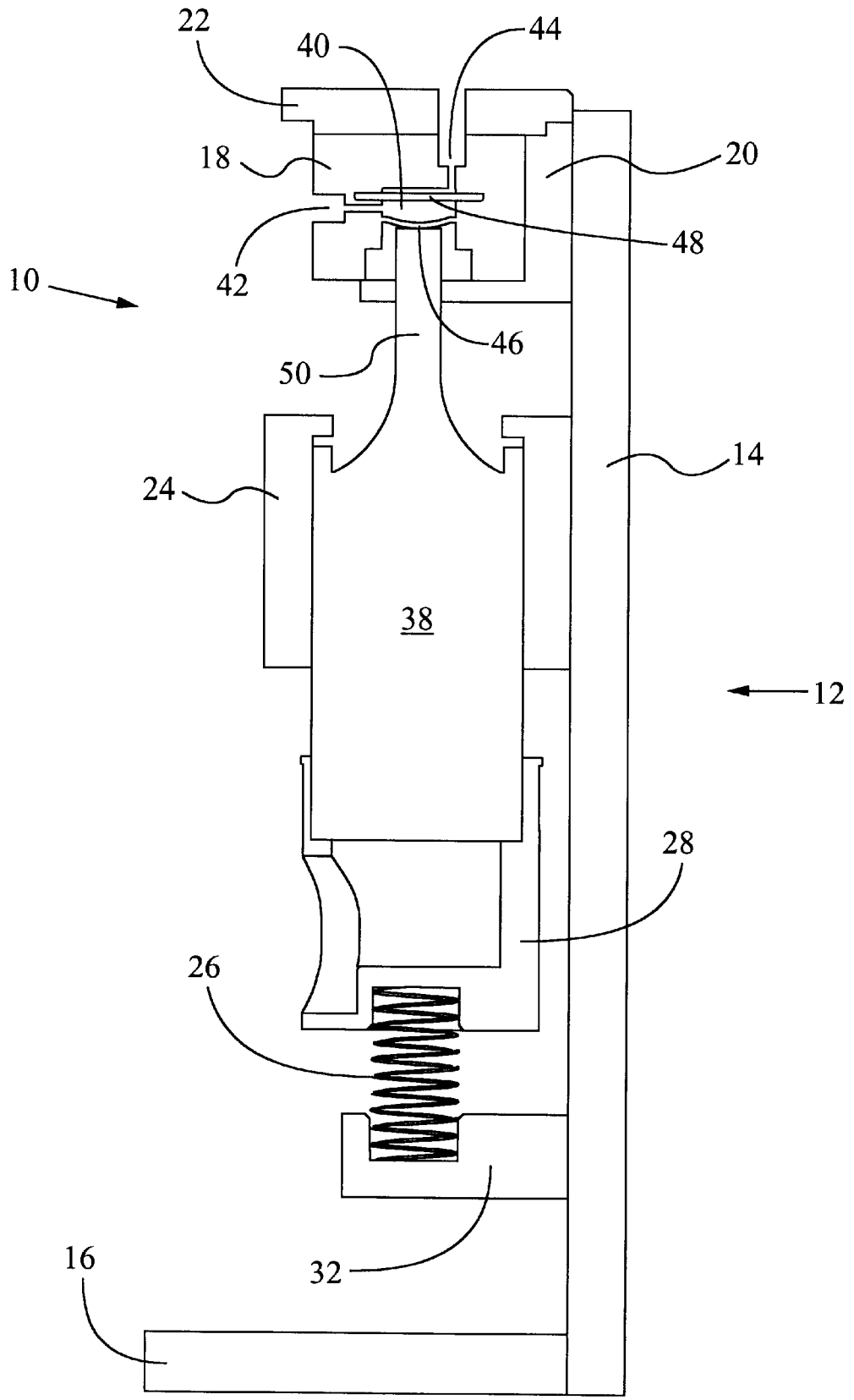
FIG. 2 is a cross sectional view of the apparatus of FIG. 1.

FIGS. 1–2 show an apparatus 10 for disrupting cells or viruses according to a first embodiment of the present invention. FIG. 1 shows an isometric view of the apparatus 10, and FIG. 2 shows a cross sectional view of the apparatus 10. As shown in FIGS. 1–2, the apparatus 10 includes a cartridge or container 18 having a chamber 40 for holding the cells or viruses. The container includes a wall 46 defining the chamber 40. The apparatus 10 also includes a transducer device 38, such as an ultrasonic horn assembly, having a vibrating surface for contacting an external surface of the wall 46 (i.e., a surface of the wall 46 that is external to the chamber 40). The wall 46 thus provides an interface between the vibrating surface of the transducer device 38 and the contents of the chamber 40. In the preferred embodiment, the wall 46 is dome-shaped and convex with respect to the transducer device 38 (i.e., the wall 46 curves outwardly towards the transducer device). The wall is preferably a structure that holds its shape when unsupported (as opposed to a flexible film or membrane), but is still sufficiently elastic to permit deflections in response to the vibrating motion of the transducer device.

As used herein, the term "transducer device" is intended to mean a device that converts electrical energy into vibrational energy. The transducer device has a vibrating surface for contacting the chamber wall 46. The transducer device 38 should be capable of vibrating at an operating frequency and amplitude sufficient to deflect the wall 46 and create pressure pulses or pressure waves in the chamber 40. In the presently preferred embodiment, the transducer device 38 is an ultrasonic horn assembly for sonicating the chamber 40. The ultrasonic horn assembly includes piezoelectric material and a horn having a vibrating tip 50 for contacting the wall 46. The horn tip 50 thus provides the vibrating surface of the transducer device. In this embodiment, the operating frequency of the transducer device is preferably the resonant frequency of the horn.

Although an ultrasonic horn assembly is presently preferred, it is to be understood that different types of transducer devices may be employed in the apparatus and method of the present invention. Suitable transducer devices include ultrasonic, piezoelectric, magnetostrictive, or electrostatic transducer devices. The transducer device may also be an electromagnetic device having a wound coil, such as a voice coil motor or a solenoid device. The operating frequency of the transducer device may be ultrasonic (i.e., above 20 kHz) or below ultrasonic (e.g., in the range of 60 to 20,000 Hz). The advantage to using higher frequencies (e.g., ultrasonic) is that cell disruption is very rapid and can often be completed in 10 to 20 seconds. The disadvantage is that ultrasonic transducer devices are often more expensive than a simple mechanical vibrator, e.g., a speaker or electromagnetic coil device.

In one alternative embodiment, the transducer device 38 comprises piezoelectric material, e.g., a piezoelectric stack made of layers of piezoelectric material. Application of an AC voltage across the piezoelectric material causes the piezoelectric material to vibrate at a suitable frequency and amplitude to disrupt the cells or viruses in the chamber 40. In this embodiment, the piezoelectric device preferably includes a top layer of material (e.g., sheet metal or mylar) that is placed in contact with the external surface of the chamber wall 46. The top layer of material thus provides the vibrating surface of the transducer device for contacting the wall. An advantage to this embodiment is that a piezoelectric stack may be made to vibrate at ultrasonic frequencies for rapid cell disruption and is considerably less expensive than an ultrasonic horn assembly.

The apparatus 10 further includes a support structure 12 for holding the container 18 and the transducer device 38 against each other such that the vibrating surface of the transducer device 38 contacts the external surface of the chamber wall 46. In this embodiment, the support structure 12 includes a base structure 14 having a stand 16. The transducer device 38 is slidably mounted to the base structure 14 by a guide 24. The guide 24 is either integrally formed with the base structure 14 or fixedly attached to the base structure. The support structure 12 also includes a holder 20 attached to the base structure 14 for holding the container 18. The holder 20 has a U-shaped bottom portion providing access to the chamber wall 46. The guide 24 and the holder 20 are arranged to hold the transducer device 38 and the container 18, respectively, such that the external surface of the wall 46 contacts the transducer device 38. The support structure 12 also includes a top retainer 22 for the container 18. The retainer 22 is U-shaped to allow access to an exit port 44 formed in the container 18.

The support structure 12 further includes an elastic body, such as a spring 26, for applying a force to the transducer device 38 to press the transducer device 38 against the wall 46. The vibrating surface of the transducer device 38 is thus coupled to the wall 46 with a preload force sufficient to create a stress within the wall 46. The spring 26 is positioned between a spring guide 32 and the base of a coupler 28 that supports the bottom of the transducer device 38. As shown in FIG. 1, the coupler 28 preferably has a window 30 through which the power cord (not shown) of the transducer device 38 may be placed. Bolts or screws 36 hold the spring guide 32 in adjustment grooves 34 formed in the base structure 14. The magnitude of the force provided by the spring 26 may be adjusted by loosening the bolts 36 holding the spring guide 32, moving the guide 32 to a new position, and retightening the bolts 36 to hold the guide 32 in the new position. Once the position of the spring 26 is adjusted to provide a suitable preload force to couple the transducer device 38 to the wall 46, it is desirable to keep the preload constant from one use of the apparatus 10 to the next.

Figure 3:
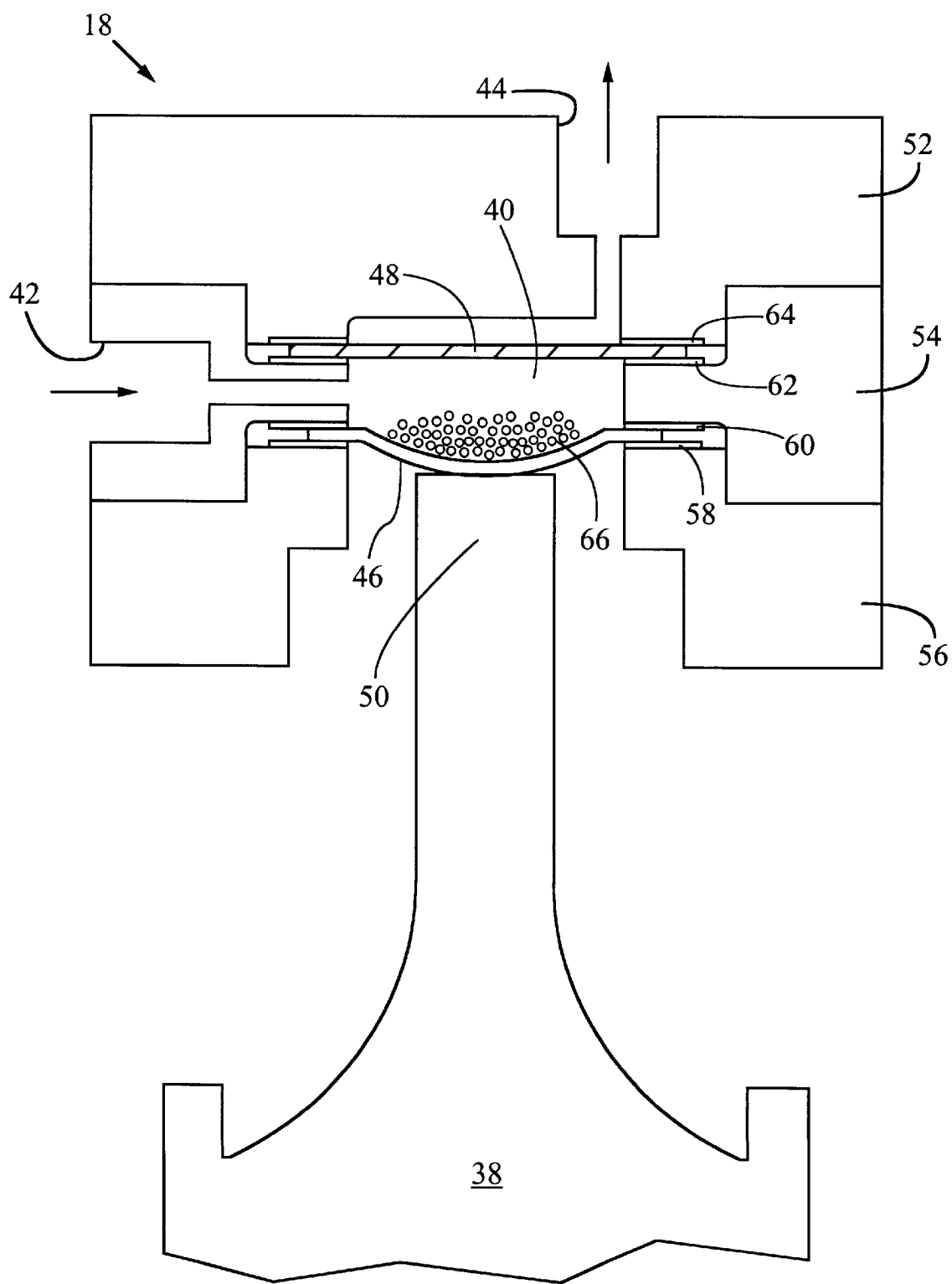
FIG. 3 is a cross sectional view of a container for use in the apparatus of FIG. 1. The vibrating surface of a transducer device is in contact with a wall of the container.

FIG. 3 shows a cross sectional view of the container 18. The container 18 has a body comprising a top piece 52, a middle piece 54, and a bottom piece 56. The middle piece 54 defines an inlet port 42 to the chamber 40, and the top piece 52 defines an outlet port 44 to the chamber. The ports 42, 44 are positioned to permit the flow of a fluid sample through the chamber 40. The wall 46 is held between the middle and bottom pieces 54, 56 using gaskets 58, 60. Alternatively, the wall 46 may simply be heat sealed to the middle piece 54 or integrally molded with the middle piece 54 so that the bottom piece 56 and gaskets 58, 60 may be eliminated. The container 18 optionally includes a filter 48 in the chamber 40 for capturing the cells or viruses to be disrupted as the sample flows through the chamber 40. Although only one filter is shown in FIG. 3, the container 18 may include multiple filters as taught in International Publication Number WO 00/73413 published Dec. 7, 2000.

To ensure that the air bubbles can escape from the chamber 40, it is desirable to use the container 18 in an orientation in which liquid flows up (relative to gravity) through the filter 48 and the chamber 40. The upward flow through the chamber 40 aids the flow of air bubbles out of the chamber. Thus, the inlet port 42 for entry of fluids into the chamber 40 should generally be at a lower elevation than the outlet port 44. The volume capacity of the chamber 40 is usually in the range of 50 to 500 $\mu$l. The volume capacity of the chamber 40 is selected to provide for concentration of analyte separated from a fluid sample without the chamber being so small that the filter 48 becomes clogged.

The pieces 52, 54, 56 forming the body of the container 18 are preferably molded polymeric parts (e.g., polypropylene, polycarbonate, acrylic, etc.). Although molding is preferred for mass production, it also possible to machine the top, middle, and bottom pieces 52, 54, 56. The pieces 52, 54, 56 may be held together by screws or fasteners. Alternatively, ultrasonic bonding, solvent bonding, or snap fit designs could be used to assemble the container 18. Another method for fabricating the container 18 is to mold the body as a single piece and heat seal the wall 46 and the filter 48 to the body.

The apparatus may optionally include beads 66 in the chamber 40 for rupturing the cells or viruses to release the intracellular material (e.g., nucleic acid) therefrom. The pressure pulses or pressure waves generated by the transducer device 38 agitates the beads 66 and movement of the beads 66 ruptures the cells or viruses. Suitable beads for rupturing cells or viruses include borosilicate glass, lime glass, silica, and polystyrene beads. The beads may be porous or non-porous and preferably have an average diameter in the range of 5 to 200 $\mu$m. In the presently preferred embodiment, the beads 66 are polystyrene beads having an average diameter of about 106 $\mu$m.

Figure 5:
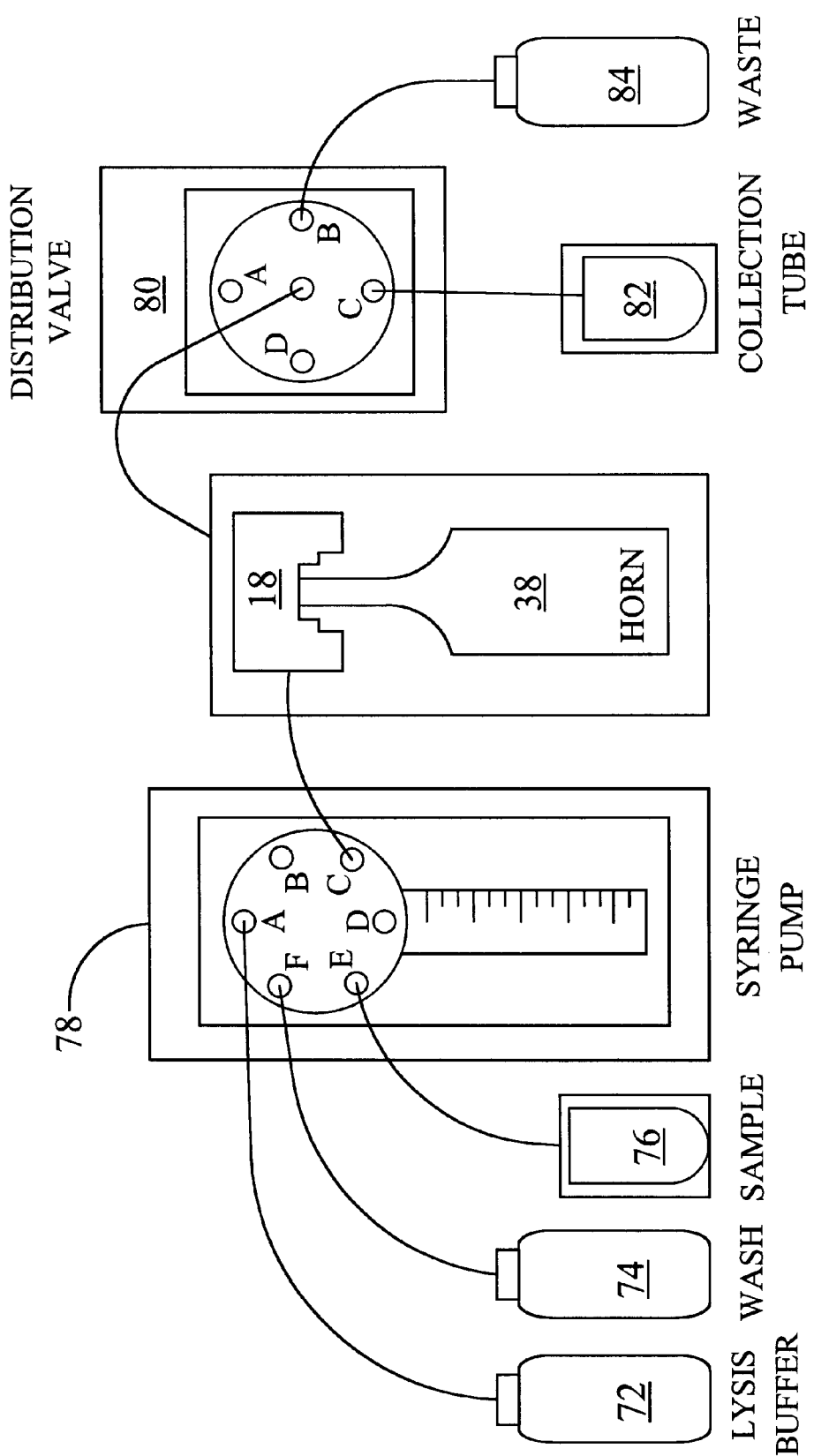
FIG. 5 is a schematic block diagram of a fluidic system incorporating the apparatus of FIG. 1.

FIG. 5 shows a fluidic system suitable for use with the apparatus. The system includes a bottle 72 for holding lysis buffer, a bottle 74 containing wash solution, and a sample container 76 for holding a fluid sample. The bottles 72, 74 and sample container 76 are connected via tubing to the valve ports of a syringe pump 78. The inlet port of the container 18 is also connected to the syringe pump 78. The outlet port of the container 18 is connected to the common port of a distribution valve 80. The system also includes a collection tube 82 for receiving intracellular material (e.g., nucleic acid) removed from the sample, and a waste container 84 for receiving waste. The collection tube 82 and waste container 84 are connected to respective peripheral ports of the distribution valve 80.

In operation, the syringe pump 78 pumps a fluid sample from the sample container 76 through the container 18 and into the waste container 84. As the fluid sample is forced to flow through the filter 48 in the chamber 40 (FIG. 3), cells or viruses in the sample are captured by the filter 48. The chamber 40 may be sonicated as the sample is forced to flow through the chamber to help prevent clogging of the filter 48. Next, the syringe pump 78 pumps wash solution from the bottle 74 through the container 18 and into the waste container 84. The washing solution washes away PCR inhibitors and contaminants from the chamber 40.

In the next step, the syringe pump 78 pumps lysis buffer from the bottle 72 into the container 18 so that the chamber 40 is filled with liquid. The lysis buffer should be a medium through which dynamic pressure pulses or pressure waves can be transmitted. For example, the lysis buffer may comprise deionized water for holding the cells or viruses in suspension or solution. Alternatively, the lysis buffer may include one or more lysing agents to aid in the disruption of the cells or viruses. One of the advantages of the present invention, however, is that harsh lysing agents are not required for successful disruption of the cells or viruses. Although it is presently preferred to separate the cells or viruses from a fluid sample using a filter as described, it is to be understood that filtration is not critical to the apparatus and method of the invention. For example, the cells or viruses to be disrupted may be placed in the chamber of the container by simply filling the chamber 40 with a liquid containing the cells or viruses (e.g., filling the chamber with an aqueous sample containing the cells or viruses to be disrupted). In this embodiment, the aqueous sample itself provides the liquid medium through which pressure waves or pressure pulses are transmitted.

Referring again to FIG. 2, the transducer device 38 is coupled to the external surface of the wall 46 with a preload force that creates a stress in the wall 46. To disrupt the cells or viruses in the chamber 40, the transducer device 38 is activated (i.e., induced into vibratory motion). As the tip 50 of the transducer device 38 vibrates, it deflects the wall 46. The interaction of the transducer device 38, chamber wall 46, and liquid in the chamber 40 is a function of the natural frequency of the wall 46, the operating frequency of the transducer device 38, the preload force between the transducer device 38 and the wall 46, and the amplitude of the vibratory motion of the transducer device 38. These parameters determine the magnitude of the pressure waves or pressure pulses generated in the chamber 40 and the resulting disruption of the cells or viruses in the chamber.

The natural frequency of the wall 46 is the frequency that causes the wall to vibrate at its highest amplitude. The preload is applied to maintain coupling between the wall 46 and the transducer device 38. The preload creates a compressive stress within the dome-shaped wall 46 that lowers its natural frequency below its natural frequency in the unstressed state. When activated, the transducer device 38 becomes a vibrating structure trapped between the wall 46 and the spring 26. The mass of the transducer device 38 combined with the spring 26 is a mass/spring system with a natural frequency dependent on the stiffness of the spring 26. The spring 26 is usually selected to provide a preload force in the range of 4 to 35 N resulting in a natural frequency of the mass/spring system of about 20 Hz, which is much less than the preferred operating frequency of the transducer device 38 (e.g., 20 to 120 kHz).

If the natural frequency of the wall 46, when the wall is stressed by the preload force, is much greater than the operating frequency of the transducer device 38, then the transducer device (when trapped between the stiff wall and the relatively weak spring) will force excitations into the spring 26. In this case, the transducer device 38 will act like a jackhammer, with the vibrating surface of the transducer device repeatedly striking the wall 46. The wall 46, however, will behave like a stiff member, deforming only slightly under the impacts. Each impact will create a slight pressure rise or pulse in the chamber 40, but no pressure drops will be created so that cavitation will be limited. Thus, when using this jackhammer technique, the vibratory motion of the transducer device is not completely transferred to the liquid in the chamber 40 and disruption of the cells or viruses, if any, will be limited. Also, the wall can be damaged (e.g., melted or cracked) by the repeated impacts.

If the natural frequency of the wall 46, when the wall is stressed by the preload force, is much less than the operating frequency of the transducer device 38, then the wall 46 will be incapable of vibrating at the same frequency as the transducer device 38. The resulting vibratory motion of the transducer device 38 and the wall 46 will become out of phase, and the wall and transducer device will physically separate, i.e., the vibrating surface of the transducer device 38 will repeatedly strike the wall 46 on its forward stroke and physically separate from the wall on its retreating stroke, much like a jackhammer.

This mode of operation can melt or damage the chamber wall, and disruption of the cells or viruses, if any, will be limited.

In accordance with the present invention, the natural frequency of the wall 46, when the wall is stressed by the preload force, should be near the operating frequency of the transducer device 38. When this is the case, the wall 46 is excited at or near its resonant frequency and the wall 46 efficiently transfers the vibratory motion of the transducer device 38 to the chamber 40 without melting or cracking. In particular, the natural frequency of the wall 46, when the wall is stressed by the preload force, should be equal to the operating frequency of the transducer device or differ from the operating frequency of the transducer device by less than 50% of the operating frequency of the transducer device, more preferably by less than 25% of the operating frequency of the transducer device, and most preferably by less than 10% of the operating frequency of the transducer device. For example, if the vibrating surface of the transducer device vibrates at an operating frequency of 40 kHz, then the natural frequency of the wall 46, when the wall is stressed by the preload force, should be in the range of 20 to 60 kHz, more preferably in the range of 30 to 50 kHz, and most preferably in the range of 36 to 44 kHz.

When the natural frequency of the wall 46, when stressed by the preload force, is tuned to the operating frequency of the transducer device 38 as described above, the transducer device 38 generates strong pressure waves or pressure pulses in the chamber 40 and strong pressure drops can be achieved in the chamber. Cavitation (the making and breaking of microscopic bubbles) usually occurs in the chamber 40. As these bubbles or cavities grow to resonant size, they collapse violently, producing very high local pressure changes. The pressure changes provide a mechanical shock to the cells or viruses, resulting in their disruption. The disruption of the cells or viruses may also be caused by sharp pressure rises resulting from the vibratory movement of the transducer device 38. In addition, the disruption of the cells or viruses may be caused by the violent motion of the beads 66 in the chamber 40. The beads are agitated by the dynamic pressure pulses or waves in the chamber and rupture the cells or viruses. The applicant has found that it is usually necessary to use beads to disrupt certain types of cells (particularly spores) having very tough cell walls. Other types of cells, such as blood cells, have weaker cell walls that may often be disrupted without the use of beads.

The chamber 40 is preferably sonicated for 10 to 20 seconds at an operating frequency in the range of 20 to 120 kHz. In the exemplary protocol, the chamber is sonicated for 15 seconds at a frequency of 40 kHz. The amplitude of the vibratory motion of the transducer device is preferably in the range of 5 to 60 μm (measured peak to peak). Referring again to FIG. 5, following disruption of the cells or viruses, the syringe pump 78 pumps the released intracellular material (e.g., nucleic acid) from the container 18 into the collection tube 82.

Figure 4:
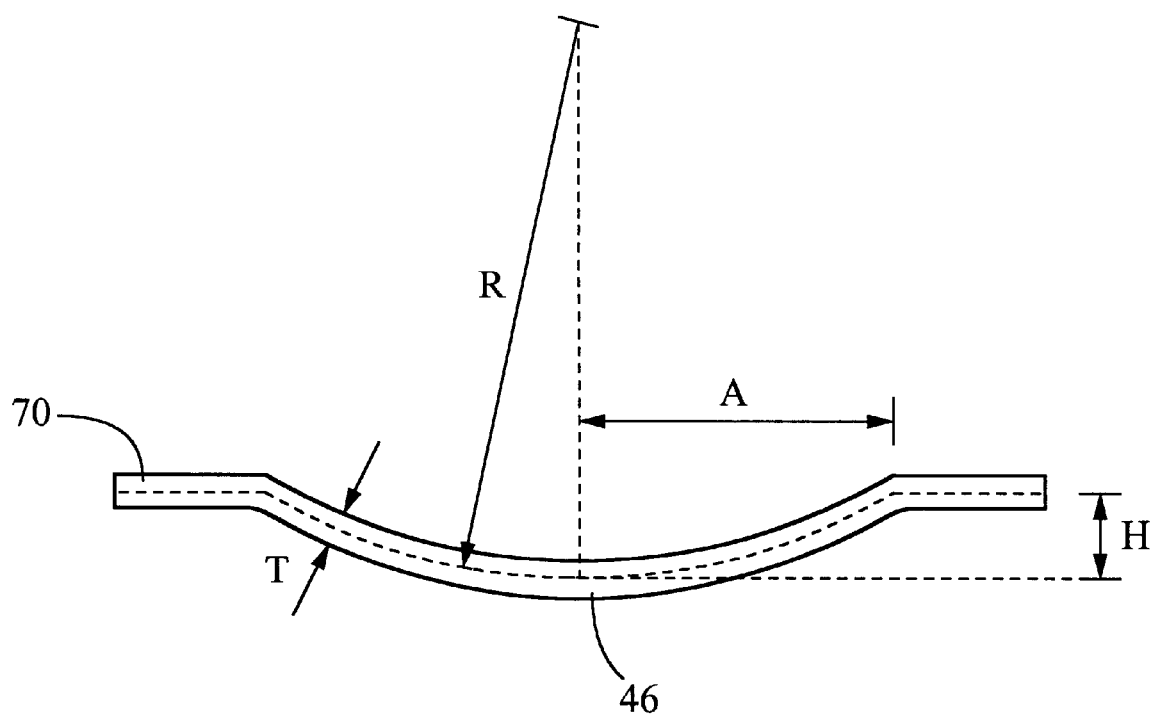
FIG. 4 is a cross-sectional view of the wall of FIG. 3.

FIG. 4 shows a cross sectional view of the wall 46. The wall 46 is dome-shaped and convex with respect to the transducer device (i.e., the wall 46 curves outwardly towards the transducer device). The advantage to the dome-shaped design of the wall 46 is that the dome shape increases the natural frequency of the wall (compared to a flat wall) without causing the wall to be so stiff that it cannot deflect to transfer the vibratory movements of the transducer device to the chamber. The dome-shaped portion of the wall is preferably spherical (i.e., has the form of a segment of a sphere). The wall 46 may also include a flat outer rim 70 for clamping the wall 46 between other pieces of the container (shown in FIG. 3). Alternatively, the wall 46 may be integrally molded with one or more pieces of the container so that the flat outer rim 70 may be eliminated. The natural frequency of the wall 46, when the wall is stressed by the preload force, is dependent upon the preload force and the following parameters of the wall: thickness T, spherical radius R, base radius A, base height or rise H, density of the wall material, modulus of elasticity, and poisson ratio.

As a first working example, the applicant had success using a dome-shaped wall having a thickness T of 0.5 mm (uniform thickness throughout wall), a spherical radius R of 12.7 mm, a base radius A of 5.16 mm, and a rise H of 1.5 mm. The wall was made of acetal (e.g., Delrin®, Du Pont Inc.) having a modulus of elasticity of 3378 N/mm$^2$, a density of 1.42 g/cm$^3$, and a poisson ratio of 0.35. The transducer device was coupled to the wall with a preload force of 8.9 N. The wall had a natural frequency of approximately 38 kHz. In this example, the transducer device was an ultrasonic horn assembly (commercially available from Sonics & Materials) having a vibrating tip for contacting the wall. The transducer device was operated for 10 to 20 seconds at an operating frequency of 40 kHz (the resonant frequency of the horn). The amplitude of the vibratory motion (measured peak to peak) was in the range of 25 to 40 µm.

As a second working example, the applicant had success using a dome-shaped wall having a thickness T of 0.5 mm (uniform thickness throughout wall), a spherical radius R of 19 mm, a base radius A of 5.16 mm, and a rise H of 1.2 mm. The wall was made of acetal (e.g., Delrin®, Du Pont Inc.) having a modulus of elasticity of 3378 N/mm$^2$, a density of 1.42 g/cm$^3$, and a poisson ratio of 0.35. The transducer device was coupled to the wall with a preload force of 4.4 N. The wall had a natural frequency of approximately 32 kHz. The transducer device was an ultrasonic horn assembly having a vibrating tip for contacting the wall. The transducer device was operated for 10 to 20 seconds at an operating frequency of 40 kHz (the resonant frequency of the horn). The amplitude of the vibratory motion (measured peak to peak) was in the range of 25 to 40 µm.

The above examples are not intended to limit the scope of the invention. Many other parameter values may be selected to satisfy the criteria that the natural frequency of the wall 46 is equal to or within 50% of the operating frequency of the transducer device. Suitable parameter values for satisfying these criteria may be selected using finite element analysis software which is widely commercially available. For example, a software package COSMOS/Works® is commercially available from Structural Research and Analysis Corporation, 12121 Wilshire Blvd. 7th Floor, Los Angeles, Calif. 90025.

In designing a suitable chamber wall, the wall thickness T is preferably in the range of 0.25 to 1 mm. If the wall thickness T is less than 0.25 mm, the wall 46 may be too weak or difficult to fabricate. If the wall thickness T is greater than 1 mm, the wall may be too stiff to deflect properly in response to the vibratory movements of the transducer device. The wall 46 is preferably a molded plastic part. Suitable materials for the wall 46 include acetal, polypropylene, or polycarbonate. Further, the operating frequency of the transducer device is preferably in the range of 20 to 120 kHz, the amplitude (peak to peak) of the vibrating surface of the transducer device is preferably in the range of 5 to 60 µm, and the preload force is preferably in the range of 2 to 50 N.

Alternative Embodiments

Although a dome-shaped chamber wall is presently preferred, the wall may have alternative shapes, such as a wall that includes stiffening ribs, is flat, or has portions of differing thickness. For example, in one alternative embodiment, the chamber wall has the form of a flat, circular disk. Application of a preload force to the flat wall creates a tensile stress that increases its natural frequency above its natural frequency in the unstressed state. The dimensions of the wall are selected such that the natural frequency of the wall, when the wall is stressed by the preload force, is equal to the operating frequency of the transducer device or differs from the operating frequency of the transducer device by less than 50% of the operating frequency of the transducer device, more preferably by less than 25% of the operating frequency of the transducer device, and most preferably by less than 10% of the operating frequency of the transducer device. In selecting dimensions for the flat chamber wall, the wall thickness is preferably in the range of 0.25 to 1 mm. If the wall thickness is less than 0.25 mm, the flat wall may be too weak. If the wall thickness is greater than 1 mm, the wall may be too stiff to deflect properly in response to the vibratory movements of the transducer device.

As a specific working example of a suitable flat wall, the wall may be in the form of a circular disk having a radius of 4.5 mm and a thickness of 0.5 mm (uniform thickness throughout wall). The wall is made of acetal (e.g., Delrin®, Du Pont Inc.) having a modulus of elasticity of 3378 N/mm$^2$, a density of 1.42 g/cm$^3$, and a poisson ratio of 0.35. The transducer device is coupled to the wall with a preload force of 4.4 N. The wall has a natural frequency of approximately 20 kHz when stressed by the preload force. The transducer device is operated for 10 to 20 seconds at an operating frequency of 20 kHz. The amplitude of the vibratory motion of the transducer device (measured peak to peak) is preferably in the range of 5 to 60 µm. This example is not intended to limit the scope of the invention, and many other parameter values may be selected (e.g., using finite element analysis software) to satisfy the criteria that the natural frequency of the wall, when the wall is stressed by the preload force, is within 50% of the operating frequency of the transducer device.

Figure 6A:
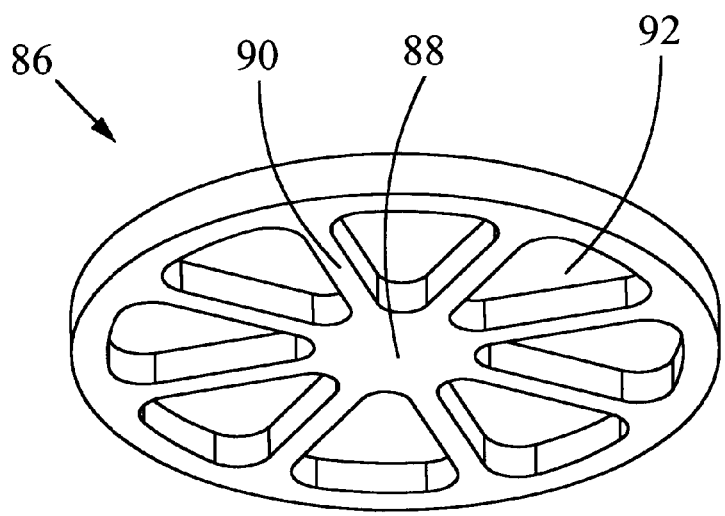
FIGS. 6A–6B are isometric views of opposite sides of another wall suitable for use in a container for holding cells or viruses to be disrupted.
Figure 6B:
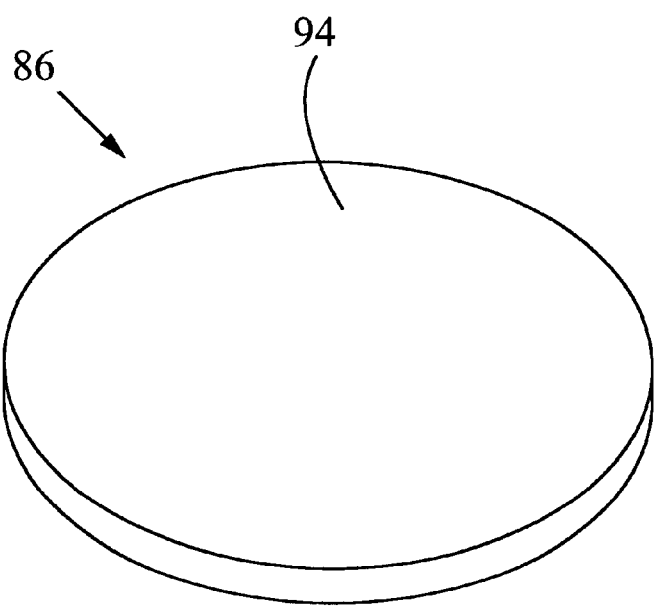
Figure 7:
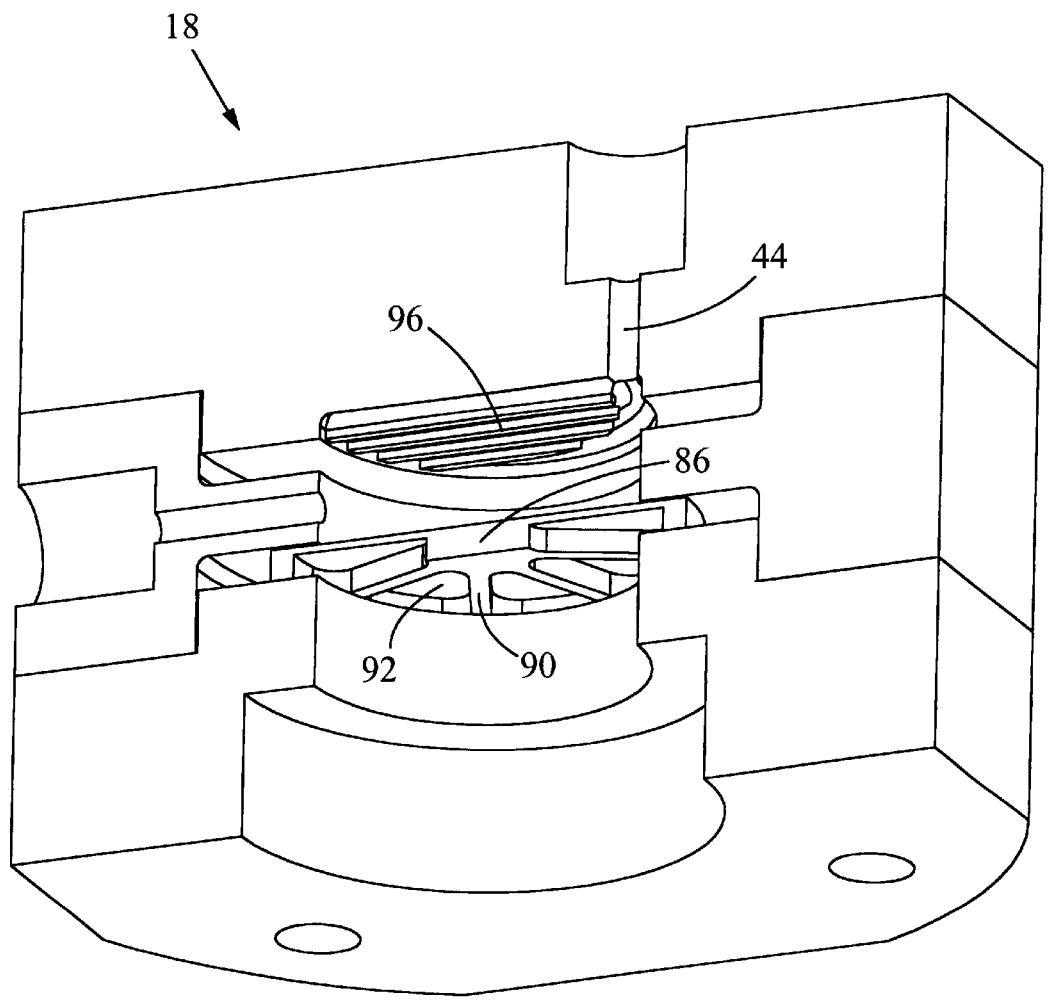
FIG. 7 is a partially cut-away, isometric view of a container incorporating the wall of FIGS. 6A–6B.

FIGS. 6A–6B illustrate another chamber wall 86 for contacting the vibrating surface of a transducer device according to the present invention. As shown in FIG. 6A, one side of the wall 86 has a central portion 88 and a plurality of stiffening ribs 90 extending radially from the central portion 88. The wall also has recesses 92 formed between the ribs 90. As shown in FIG. 6B, the other side of the wall 86 has a flat surface 94. FIG. 7 shows a partially-cut away, isometric view of the container 18 with the wall 86. The wall 86 is preferably positioned so that the side of the wall having the flat surface is internal to the chamber and such that the side of the wall having the ribs 90 is external to the chamber. The ribs 90 are advantageous because they increase the natural frequency of the wall 86 (as compared to a flat wall) without causing the wall to be so stiff that it cannot deflect in response to the vibratory movements of the transducer device.

Figure 8:
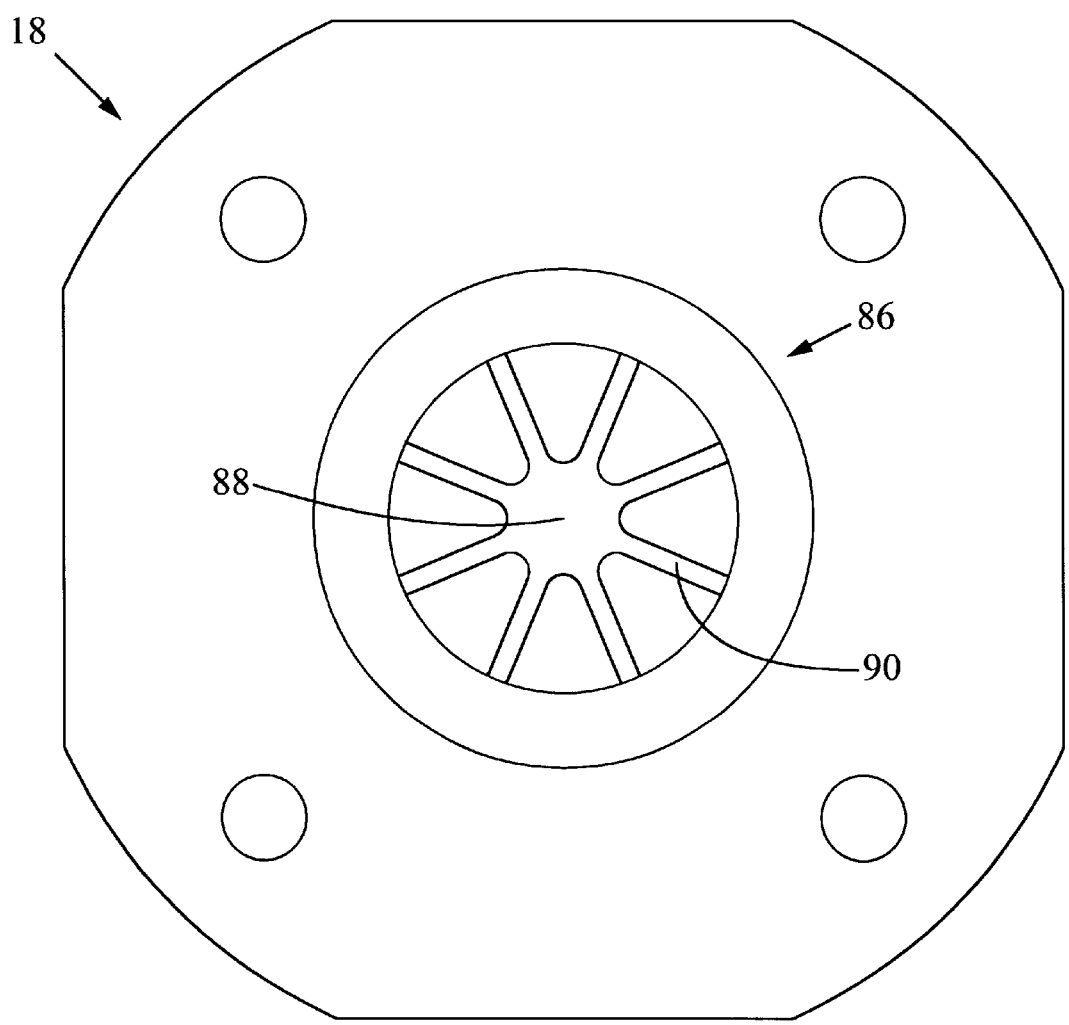
FIG. 8 is a bottom plan view of the container of FIG. 7.

FIG. 8 shows a bottom plan view of the container 18 having the wall 86. The central portion 88 provides the external surface of the wall 86 for contacting a transducer device. The dimensions of the wall 86 are selected to satisfy the criteria that the natural frequency of the wall, when stressed by the preload force, is equal to or within 50% of the operating frequency of the transducer device, more preferably within 25% of the operating frequency of the transducer device, and most preferably within 10% of the operating frequency of the transducer device. Suitable wall dimensions for satisfying these criteria may be selected using finite element analysis software (e.g., COSMOS/Works® commercially available from Structural Research and Analysis Corporation). The wall 86 is preferably a molded plastic part. Suitable materials for the wall 86 include acetal, polypropylene, or polycarbonate.

Referring again to FIG. 7, the interaction of the ribbed wall 86 with the transducer device is similar to the interaction of the dome-shaped wall with the transducer device described above. The vibrating surface of a transducer device is coupled to the external surface of the wall 86 (preferably coupled to the central portion of the wall) with a preload force that creates a stress in the wall, typically a mixture of compressive and tensile stresses. To disrupt the cells or viruses in the chamber of the container 18, the transducer device is activated and the vibrating surface of the transducer device deflects the wall 86. When the natural frequency of the wall 86, when stressed by the preload force, is tuned to the operating frequency of the transducer device as described above, the transducer device generates strong pressure waves or pressure pulses in the chamber and strong pressure drops can be achieved in the chamber. Cavitation usually occurs resulting in the disruption of the cells or viruses in the chamber. In addition, the disruption of the cells or viruses may optionally be caused by the violent motion of the beads in the chamber.

The chamber is preferably sonicated for 10 to 20 seconds at an operating frequency in the range of 20 to 120 kHz. In the exemplary protocol, the chamber is sonicated for 15 seconds at a frequency of 40 kHz. The amplitude of the vibratory motion of the transducer device is preferably in the range of 5 to 60 μm (measured peak to peak). The top wall of the chamber may optionally have flow ribs 96. The flow ribs 96 are useful for channeling liquid and air bubbles out of the chamber through outlet port 44.

The container for holding the cells or viruses need not be the specific container described in the preferred embodiment above. Any type of container having a chamber for holding the cells or viruses may be used to practice the invention, as long as the container is fabricated with a suitable chamber wall in accordance with the principles of the present invention. Suitable containers include, but are not limited to, reaction vessels, cuvettes, cassettes, and cartridges. The container may have multiple chambers and/or channels for performing multiple sample preparation and analysis functions, e.g., amplifying and detecting the nucleic acid released from the lysed cells or viruses. Such containers are disclosed in International Application Number PCT/US00/14738 filed May 30, 2000 and in International Application Number PCT/US01/23776 filed Jul. 26, 2001. Alternatively, the container may have only a single chamber for holding cells or viruses for disruption.

There are many different possible means for coupling the vibrating surface of a transducer device to the chamber wall with a preload force according to the apparatus and method of the present invention. For example, in one alternative embodiment, the coupling means comprises a vise or clamp for pressing the transducer device and container against each other. In another embodiment, the coupling means comprises an instrument or appliance into which the container is placed for sample processing. The instrument includes a nesting site for receiving the container, and the transducer device is positioned in the instrument such that the vibrating surface of the transducer device is adjacent the external surface of the chamber wall when the container is placed in the nesting site. The instrument may include an elastic body (e.g., spring) for providing the preload force to press the transducer device against the chamber wall. Alternatively, the transducer device may simply be rigidly fixed in the instrument and the container is clamped against the surface of the transducer device to provide the preload force, e.g., by closing a lid over the container.

In another embodiment, the coupling means comprises a pressure system for applying air pressure to press together the transducer device and the container. Alternatively, magnetic or gravitational force may be used to couple the transducer device and the container with the preload force. In each embodiment of the invention, force may be applied to the transducer device (or a holder in which the transducer device is placed), to the container (or a holder in which the container is placed), or to both the transducer device and the container.

In embodiments in which an elastic body is used to provide the preload force between the transducer device and chamber wall, suitable elastic bodies include, but are not limited to, coil springs, wave springs, torsion springs, spiral springs, leaf spring, elliptic springs, half-elliptic springs, rubber springs, and atmospheric springs. Preferably, the elastic body is a coil spring. Coil springs are preferred because they are simple and inexpensive to place in the apparatus. In addition, in each of these embodiments, the elastic body may be positioned to either push or pull the transducer device and container towards each other. For example, a spring may be positioned to provide the preload force by either pushing or pulling. Further, multiple elastic bodies may be employed to apply forces.

Moreover, in any of the embodiments of the invention, gel or liquid may be provided on the vibrating surface of the transducer device or external surface of the chamber wall to improve contact between the two.

Therefore, the scope of the invention should be determined by the following claims and their legal equivalents.

What is claimed is:

1. A method for disrupting cells or viruses, the method comprising the steps of:
   a) holding a liquid or gel containing the cells or viruses in the chamber of a container, wherein the container includes at least one wall defining the chamber, and wherein the wall has a surface external to the chamber;
   b) coupling a transducer device to the external surface of the wall with a preload force sufficient to create a stress within the wall; and
   c) operating the transducer device at a frequency and amplitude sufficient to generate pressure waves or pressure pulses in the chamber;
   wherein the natural frequency of the wall, when the wall is stressed by the preload force, is equal to the operating frequency of the transducer device or differs from the operating frequency of the transducer device by less than 50% of the operating frequency of the transducer device.

2. The method of claim 1, wherein the operating frequency is ultrasonic.

3. The method of claim 1, wherein to transducer device comprises an ultrasonic horn having a tip for contacting the wall, and wherein the operating frequency is the resonant frequency of the horn.

4. The method of claim 1, further comprising the step of agitating beads in the chamber to rupture the cells or viruses.

5. The method of claim 1, further comprising the step of positioned forcing a fluid sample taming the cells or viruses to flow through the chamber.

6. The method of claim 1, wherein the natural frequency of the wall, when the wall is stressed by the preload force, is equal to the operating frequency of the transducer device or differs from the operating frequency of the transducer device by less than 25% oft operating frequency of the transducer device.

7. The method according to claim 6, wherein the natural frequency of the wall, when the wall is stressed by the preload force, is less than the operating frequency of the transducer device by within 25% of the operating frequency or equal to the operating frequency of the transducer device.

8. The method of claim 1, wherein the natural frequency of the wall, when the wall is stressed by the preload force, is equal to the operating frequency of the transducer device or differs from to operating frequency of the transducer device by less than 10% of operating frequency of the transducer device.

9. The method according to claim 8, wherein the natural frequency of the wall, when the wall is stressed by the preload force, is less than the operating frequency of the transducer device by within 10% of the operating frequency or equal to the operating frequency of the transducer device.

10. The method according to claim 1, wherein the natural frequency of the wall, when the wall is stressed by the preload force, is less than the operating frequency of the transducer device by within 50% of the operating frequency or equal to the operating frequency of the transducer device.

11. The method of claim 1, wherein the operating frequency of the transducer device is in the range of 20 to 120 kHz, the amplitude of the vibratory motion of the transducer device is in the range of 5 to 60 micrometers, and the preload force is in the range of 2 to 50 N.

12. An apparatus for disrupting cells or viruses, the apparatus comprising:
   a) a container having a chamber for holding the cells or viruses, wherein the container includes at least one wall defining the chamber, and wherein the wall has a surface external to the chamber;
   b) a transducer device for vibrating at an operating frequency and amplitude sufficient to generate pressure waves or pressure pulses in the chamber when the transducer device is coupled to the wall; and
   c) means for coupling the transducer device to the external surface of the wall with a preload force sufficient to create a stress within the wall;
   wherein the natural frequency of the wall, when the wall is stressed by the preload force, is equal to the operating frequency of the transducer device or differs from the operating frequency of the transducer device by less than 50% of the operating frequency of the transducer device.

13. The apparatus of claim 12, wherein the operating frequency is ultrasonic.

14. The apparatus of claim 13, wherein the transducer device comprises an ultrasonic horn having a tip that is coupled to the wall, and wherein the operating frequency is the resonant frequency of the horn.

15. The apparatus of claim 12, wherein the transducer device comprises a piezoelectric stack.

16. The apparatus of claim 12, wherein the wall is dome-shaped and convex with respect to the transducer device.

17. The apparatus of claim 12, wherein the wall is spherical and convex with respect to the transducer device.

18. The apparatus of claim 12, wherein the wall is flat.

19. The apparatus of claim 12, wherein the wall includes a central portion and stiffening ribs extending radially from the central portion.

20. The apparatus of claim 12, further comprising beads in the chamber for rupturing the cells or viruses.

21. The apparatus of claim 12, wherein the chamber has at least two ports positioned to permit flow of a sample trough to chamber, and wherein the apparatus further comprises a filter in the chamber for capturing to cells or viruses as the sample flows through the chamber.

22. The apparatus of claim 12, wherein to natural frequency of the wall, when the wall is stressed byte preload force, is equal to the operating frequency of the transducer device or differs from the operating frequency of the transducer device by less than 25% of the operating frequency of the transducer device.

23. The apparatus according to claim 22, wherein the natural frequency of the wall, when the wall is stressed by the preload force, is less than the operating frequency of the transducer device by within 25% of the operating frequency or equal to the operating frequency of the transducer device.

24. The apparatus of claim 12, wherein the natural frequency of the wall, when to wall is stressed by the preload force, is equal to the operating frequency of the transducer device or differs from the operating frequency of the transducer device by less than 10% of the operating frequency of to transducer device.

25. The apparatus according to claim 24, wherein the natural frequency of the wall, when the wall is stressed by the preload force, is less than the operating frequency of the transducer device by within 10% of the operating frequency or equal to the operating frequency of the transducer device.

26. The apparatus according to claim 12, wherein the natural frequency of the wall, when to wall is stressed by to preload force, is less than the operating frequency of to transducer device by within 50% of the operating frequency or equal to the operating frequency of the transducer device.

27. The apparatus of claim 12, wherein to operating frequency of to transducer device is in the range of 20 to 120 kHz, the amplitude of the vibratory motion of the transducer device is in the range of 5 to 60 micrometers, and to preload force is in the range of 2 to 50 N.

28. The apparatus of claim 12, wherein the means for coupling the transducer device to the wall comprises a support structure for holding the container and the transducer device against each other such that the vibrating surface of the transducer device contacts the external surface of the wall, the support structure including an elastic body for providing the preload force.

29. The apparatus of claim 28, wherein the elastic body comprises a spring.

30. The apparatus of claim 12, wherein the means for coupling the vibrating surface of the transducer device to the wall comprises a clamp.

* * * * *

UNITED STATES PATENT AND TRADEMARK OFFICE
CERTIFICATE OF CORRECTION

| | | |
|---|---|---|
| PATENT NO. | : 6,739,531 B2 | |
| APPLICATION NO. | : 09/972221 | |
| DATED | : May 25, 2004 | |
| INVENTOR(S) | : Michael T. Taylor | |

It is certified that error appears in the above-identified patent and that said Letters Patent is hereby corrected as shown below:

In claim 3, column 12, line 53, please delete "to" and insert --the--.

In claim 5, column 12, line 60, please delete "positioned" and insert --capturing the cells or viruses on at least one filter positioned in the chamber by--.

In claim 5, column 12, line 60, please delete "taming" and insert --containing--.

In claim 6, column 12, line 66, please delete "oft" and insert --of the--.

In claim 8, column 13, line 9, please delete "to" and insert --the--.

In claim 21, column 14, line 9, please delete "trough to" and insert --through the--.

In claim 21, column 14, line 10, please delete "to" and insert --the--.

In claim 22, column 14, line 12, please delete "to" and insert --the--.

In claim 22, column 14, line 13, please delete "byte" and insert --by the--.

In claim 24, column 14, line 25, please delete "to" and insert --the--.

In claim 26, column 14, line 37, please delete "to wall is stressed by to" and insert --the wall is stressed by the--.

In claim 26, column 14, line 38, please delete "to" and insert --the--.

In claim 27, column 14, line 41, please delete "to" and insert --the--.

In claim 27, column 14, line 42, please delete "of to" and insert --of the--.

UNITED STATES PATENT AND TRADEMARK OFFICE
CERTIFICATE OF CORRECTION

PATENT NO.       : 6,739,531 B2
APPLICATION NO.  : 09/972221
DATED            : May 25, 2004
INVENTOR(S)      : Michael T. Taylor It is certified that error appears in the above-identified patent and that said Letters Patent is hereby corrected as shown below:

In claim 27, column 14, line 44, please delete "and to" and insert --and the--.

Signed and Sealed this

Twenty-first Day of April, 2009

JOHN DOLL
*Acting Director of the United States Patent and Trademark Office*